United States Patent
Beyer et al.

(10) Patent No.: US 11,746,333 B2
(45) Date of Patent: Sep. 5, 2023

(54) CONTINUOUSLY BIOPRINTED MULTILAYER TISSUE STRUCTURE

(71) Applicant: ASPECT BIOSYSTEMS LTD., Vancouver (CA)

(72) Inventors: Simon Beyer, Richmond (CA); Tamer Mohamed, Richmond (CA); Sheng Pan, Vancouver (CA); Sam Wadsworth, Vancouver (CA)

(73) Assignee: ASPECT BIOSYSTEMS LTD.

(*) Notice: Subject to any disclaimer, the term of this patent is extended or adjusted under 35 U.S.C. 154(b) by 0 days.

(21) Appl. No.: 15/736,743

(22) PCT Filed: Jun. 16, 2016

(86) PCT No.: PCT/CA2016/050707
§ 371 (c)(1),
(2) Date: Dec. 14, 2017

(87) PCT Pub. No.: WO2016/201577
PCT Pub. Date: Dec. 22, 2016

(65) Prior Publication Data
US 2018/0171304 A1    Jun. 21, 2018

Related U.S. Application Data

(60) Provisional application No. 62/305,422, filed on Mar. 8, 2016, provisional application No. 62/180,174, filed on Jun. 16, 2015.

(51) Int. Cl.
*C12N 5/071* (2010.01)
*C12N 5/077* (2010.01)
(Continued)

(52) U.S. Cl.
CPC .......... *C12N 5/0697* (2013.01); *B29C 64/118* (2017.08); *B33Y 70/00* (2014.12);
(Continued)

(58) Field of Classification Search
CPC ... C12N 5/0697; C12N 5/0658; B29C 64/118; G01N 33/5061; B33Y 80/00; B33Y 70/00; C12M 21/08; C12M 25/14
See application file for complete search history.

(56) References Cited

U.S. PATENT DOCUMENTS 6,139,574 A    10/2000  Vacanti et al.
7,051,654 B2   5/2006   Boland et al.
(Continued)

FOREIGN PATENT DOCUMENTS

WO    WO 2011/116125 A2    9/2011
WO    WO 2013/040078 A1    3/2013
WO    WO 2014/197999 A1    12/2014

OTHER PUBLICATIONS

Raghavan et al. Bioengineered Three-Dimensional Physiological Model of Colonic Longitudinal Smooth Muscle In Vitro. Tissue Engineering: Part C. vol. 16, No. 5, 2010. p. 999-1009 (Year: 2010).*

(Continued)

*Primary Examiner* — Taeyoon Kim
(74) *Attorney, Agent, or Firm* — Todd Lorenz

(57) ABSTRACT

Provided herein are synthetic living tissue structures comprising multiple layers of fibers deposited in solidified form from a 3D bioprinter, together with kits and methods of use related thereto. The fibers comprise a plurality of mammalian cells dispensed within a solidified biocompatible matrix. The structural integrity of the fiber is maintained upon and after deposition without any additional crosslinking. The fiber is continuously bioprinted through at least two layers of the structure. In one aspect, synthetic muscle tissue structures exhibit a readily assayable contractile functionality.

13 Claims, 3 Drawing Sheets

(51) Int. Cl.
*C12M 1/12* (2006.01)
*G01N 33/50* (2006.01)
*B33Y 80/00* (2015.01)
*B33Y 70/00* (2020.01)
*C12M 1/26* (2006.01)
*C12M 3/00* (2006.01)
*B29C 64/118* (2017.01)
*B33Y 10/00* (2015.01)

(52) U.S. Cl.
CPC .............. *B33Y 80/00* (2014.12); *C12M 21/08* (2013.01); *C12M 25/14* (2013.01); *C12M 33/00* (2013.01); *C12N 5/0658* (2013.01); *G01N 33/5061* (2013.01); *B33Y 10/00* (2014.12); *C12N 2533/50* (2013.01)

(56) References Cited

U.S. PATENT DOCUMENTS

| | | | |
|---|---|---|---|
| 7,368,279 | B2 | 5/2008 | Bitar et al. |
| 8,691,274 | B2 | 4/2014 | Xu et al. |
| 8,931,880 | B2 | 1/2015 | Murphy et al. |
| 9,005,972 | B2 | 4/2015 | Xu et al. |
| 9,149,952 | B2 | 10/2015 | Murphy et al. |
| 9,227,339 | B2 | 1/2016 | Murphy et al. |
| 9,301,925 | B2 | 4/2016 | Xu et al. |
| 9,315,043 | B2 | 4/2016 | Murphy et al. |
| 2006/0105011 | A1* | 5/2006 | Sun .................. B29C 64/112 424/422 |
| 2009/0263849 | A1* | 10/2009 | Sun .................. B01L 3/502707 435/29 |
| 2012/0089238 | A1 | 4/2012 | Kang et al. |
| 2013/0164339 | A1 | 6/2013 | Murphy et al. |
| 2013/0345794 | A1 | 12/2013 | Khatiwala et al. |
| 2014/0287960 | A1 | 9/2014 | Shepherd et al. |
| 2014/0377232 | A1 | 12/2014 | Bitar |
| 2016/0297104 | A1* | 10/2016 | Guillemette .......... B29B 11/16 |

OTHER PUBLICATIONS

Grosberg et al. Muscle on a Chip: In Vitro Contractility Assays for Smooth and Striated Muscle. J Pharmacol Toxicol Methods. 2012; 65(3): 126-135 (Year: 2012).*
Zhang et al. In Vitro Study of Directly Bioprinted Perfusable Vasculature Conduits. Biomater Sci. Jan. 1, 2015; 3(1): 134-143 (Year: 2015).*
Tan et al. Direct bioprinting of alginate-based tubular contructs using multi-nozzle extrusion-based technique. 1st International Conference on Progress in Additive Manufacturing (Pro-AM 2014) May 26-28, 2014, Singapore. (Year: 2014).*
Ghorbanian, S. and Junker, D., "Microfluidic Probe for Direct Write of Soft Cell Scaffolds," Thesis for Master of Engineering, Micro and Nanobioengineering Laboratory Department of Biomedical Engineering Faculty of Medicine, McGill University (2010).
Jakab et al., "Three-dimentional tissue constructs built by bioprinting," Biotheology, vol. 43, pp. 509-513 (2006).
Kim et al., "Scaffolds for engineering smooth muscle under cyclic mechanical strain conditions," J. Biomech Eng, vol. 122(3), pp. 210-215 (2000).
Lai et al., "Phenotypic and functional characteristics of in vivo tissue engineered smooth muscle from normal and pathological bladders," Journal of Urology, vol. 168, pp. 1853-1858 (2002).
Manucol® LD sodium alginate Product Specifications and Analysis Data Sheet, FMC BioPolymer (2012-2014).
Markstedt et al., "3D Bioprinting Human Chondrocytes with Nanocellulose-Alginate Bioink for Cartilage Tissue Engineering Applications," BioMacromolecules, vol. 16, pp. 1489-1496 (2015).
Nesmith et al., "Human airway musculature on a chip: an in vitro model of allergic asthmatic bronchoconstriction and bronchodilation," Lab Chip, vol. 14, No. 20, pp. 3925-3936 (2014).
Norotte et al., "Scaffold-Free Vascular Tissue Engineering Using Bioprinting," Biomaterials, vol. 30(30), pp. 5910-5917, (2009).
Torihasi et al., Acute and Temporal Expression of Tumor Necrosis Factor (TNF)-α-stimulated Gene 6 Product, TSG6, in Mesenchymal Stem Cells creates microenvironments Required for their Successful Transplantation into Muscle Tissue, J of Biol. Chemistry, vol. 190, No. 37, pp. 22771-22781 (2015).
Yu et al. "Tissue Strands as "Bioink" for Scale-up Organ Printing," Conf. Proc. IEEE Eng Med Biol. Soc. 2014, pp. 1428-1431 (2014).

* cited by examiner time = 0      time = 40 min

CONTINUOUSLY BIOPRINTED MULTILAYER TISSUE STRUCTURE

CROSS-REFERENCE TO RELATED APPLICATIONS

This application claims the benefit of U.S. Provisional Application Ser. No. 62/180,174 filed Jun. 16, 2015, and also U.S. Provisional Application Ser. No. 62/180,174 filed Mar. 8, 2016, both of which are hereby incorporated by reference in their entirety.

FIELD OF THE INVENTION

The invention relates to bioengineered tissue containing muscle cells for the purpose of testing muscle contraction and relaxation in response to different stimuli. The invention also relates to bioprinting methods for fabricating such tissue.

BACKGROUND OF THE INVENTION

The skeletal muscle system represents a fundamental part of the basic architecture and functionality of the body, while smooth muscle plays an important role in many biological systems such as the vascular, respiratory, lymphatic, and gastrointestinal systems, and is also found in the skin, eye, bladder and several other organs. Both types of tissues play a critical role in many diseases related to these systems. As such it is important for researchers from academia and the pharmaceutical industry to have access to physiologically relevant tissue models to gain a better understanding of disease pathways and basic physiology by testing the response of skeletal and smooth muscle tissue to various compounds or other stimuli.

Previous attempts at creating such models have been made and typically include moulding cells, either suspended in a matrix or formed into aggregates, into a particular form using a mould, or seeding cells onto the outside of a previously formed scaffold. Although the most advanced models are able to recapitulate certain functions of smooth muscle tissue, such as contraction, their fabrication is manually intensive, leading to challenges in reproducibility. In other models the fabrication is less complicated but the ability of the tissue to contract is lost.

More recently, 3D printing, a form of additive manufacturing (AM), has been applied to create three-dimensional objects directly from digital files, wherein the object is built up layer-by-layer to achieve the desired three dimensional structure. Initial efforts to adapt 3D printing techniques to the creation of cellular constructs and tissues, termed 3D bioprinting, also focused on initial printing of scaffold materials independent of the direct seeding or subsequent printing of the cellular materials, consistent with the above convention. See, e.g. U.S. Pat. Nos. 6,139,574; 7,051,654; 8,691,274; 9,005,972 and 9,301,925. Unfortunately, however, the polymers typically employed to form the prior art scaffolds, while generally considered biocompatible, are not physiologically compatible. As such, cell viability is sacrificed with this approach in favor of the mechanical stability of the requisite scaffold.

Alternative 3D bioprinting techniques have also been described emphasizing the converse, wherein mechanical structure and shape fidelity are sacrificed in favor of cell viability. These bioprinting systems create synthetic tissues by dispensing cellular materials within a biocompatible matrix, which is then cross-linked or otherwise solidified after deposition to create a solid or semi-solid tissue structure. See, e.g., U.S. Pat. Nos. 9,227,339; 9,149,952; 8,931,880 and 9,315,043; U.S. Patent Publication Nos. 2012/0089238; 2013/0345794; 2013/0164339 and 2014/0287960. With all of these systems, however, the temporal delay between the deposition and crosslinking steps invariably leads to a lack of control over the geometry of the printed structure, as well as the cellular and matrix composition of the structure. Moreover, cellular viability is often still compromised in any event by the subsequent cross-linking or solidification event.

As but one example of this problem, Markstedt et al. described a system in which hydrogels, such as collagen, hyaluronic acid, chitosan and alginate were used in combination with non-physiologic reinforcing fiber materials, such as nanofibrillated cellulose, as a bio-ink for 3D bioprinting. *BioMacromolecules* 16:1489-96 (2015). This bio-ink is deposited as a 2D layer of material, which is submerged in a divalent cation bath ($CaCl_2$) to crosslink for ten minutes and solidify the first layer before depositing another layer on top. Although living cells were successfully incorporated into their bio-ink, a cell viability analysis demonstrated that the cell viability decreased significantly as a result of the cross-linking process, from ~95.3% before embedding, to ~69.9% after embedding and crosslinking. Furthermore, a comparison to non-printed controls revealed that the decrease in cell viability was likely due to the preparation and mixing of the bio-ink itself, rather than the actual 3D printing process.

Accordingly, existing 3D bioprinting techniques and materials have failed to satisfactorily resolve the technical conflict between structural integrity and shape fidelity on the one hand, and physiological compatibility and cellular viability on the other. The current invention addresses these and other unmet needs.

PRIOR ART

Literature

Cyrille Norotte, Francois S. Marga, Laura E. Niklason, and Gabor Forgacs, "Scaffold-free vascular tissue engineering using bioprinting", *Biomaterials*, Vol. 30, 2009, pp. 5910-5917.

Jin-yau Lai, Cheol Yong Yoon, James J. Yoo, Tina Wulf, and Anthony Atala, "Phenotypic and functional characteristics of in vivo tissue engineered smooth muscle from normal and pathological bladders", *Journal of Urology*, Vol. 168, 2002, pp. 1853-1858.

Byung-Soon Kim, and David J. Mooney "Scaffolds for engineering smooth muscle under cyclic mechanical strain conditions", *J. Biomech Eng*, Vol. 122(3_, 2000, pp. 210-215.

Patents

US20140287960
US20130345794
US20140377232
U.S. Pat. No. 7,368,279

SUMMARY OF INVENTION

The present invention successfully resolves the previously conflicting objectives in the 3D bioprinting art between structural integrity and cellular viability, providing synthetic living tissue structures deposited in solidified form with improved cell survival and physiological functionality, and without the need for cross-linking or other subsequent solidification steps. Aspects of the present invention include synthetic living tissue structures comprising a synthetic tissue fiber comprising a plurality of mammalian cells dispensed from a bioprinter within a solidified biocompatible matrix, wherein the structural integrity of the fiber is maintained upon and after deposition, and without any additional cross-linking step(s). In preferred embodiments, the invention provides synthetic living tissue structures comprising overlapping layers of a continuous synthetic tissue fiber, wherein the overlapping layers can be structurally discrete. In specific embodiments, synthetic muscle tissue structures are provided comprising two or more layers of a continuous synthetic tissue fiber comprising a plurality of mammalian muscle cells dispensed from a bioprinter within a solidified biocompatible matrix.

In one aspect, the invention provides a synthetic living tissue structure comprising a synthetic tissue fiber dispensed from a bioprinter, the fiber comprising a plurality of mammalian cells dispensed from a bioprinter within a solidified biocompatible matrix, wherein the structural integrity of the fiber is maintained after dispensation from the printhead, and without having to cross-link the matrix after contacting the deposition surface. In preferred embodiments, the invention provides synthetic living tissue structures comprising a continuous overlapping fiber of mammalian cells dispensed from a bioprinter and dispersed within a biocompatible matrix, wherein said fiber is continuously bioprinted through at least two or more layers of the structure, more preferably through at least three or four layers, still more preferably through at least five, six, seven, eight, nine, ten or more layers of the tissue structure. The mammalian cells are preferably comprised within a solidified biocompatible matrix capable of maintaining the structural integrity and shape fidelity of the fiber, such that there is a visual border between the overlapping segments of the fiber.

The solidified biocompatible matrix may comprise any of a wide variety of natural or synthetic polymers that support the viability of living cells, including, e.g., alginate, laminin, fibrin, hyaluronic acid, poly(ethylene) glycol based gels, gelatin, chitosan, agarose, or combinations thereof In preferred embodiments, the solidified biocompatible matrix comprises alginate, or other suitable biocompatible polymers that can be instantaneously solidified while dispensing from the printhead.

In particularly preferred embodiments, the solidified biocompatible matrix is physiologically compatible, i.e., conducive to cell growth, differentiation and communication. In some such embodiments, the physiologically compatible matrix comprises alginate in combination with one or more of: collagen, fibronectin, thrombospondin, glycosaminoglycans (GAG), deoxyribonucleic acid (DNA), adhesion glycoproteins, elastin, and combinations thereof. In specific embodiments, the collagen is selected from the group consisting of: collagen I, collagen II, collagen III, collagen IV, collagen V, collagen VI, or collagen XVIII. In specific embodiments, the GAG is selected from the group consisting of: hyaluronic acid, chondroitin-6-sulfate, dermatan sulfate, chondroitin-4-sulfate, or keratin sulfate.

In the preferred embodiments exemplified herein, the mammalian cells comprise muscle cells, e.g. smooth muscle cells, skeletal muscle cells and/or cardiac muscle cells. In alternative embodiments, the tissue or tissue structure further comprises at least one additional cell type, e.g. fibroblasts, endothelial and/or epithelial cells, stem cells etc. In one such embodiment, the at least one additional cell type is dispersed within said fiber. In another such embodiment, the at least one additional cell type is disposed concentrically around the outside of said fiber as an external/second layer. In particularly preferred embodiments, the mammalian cells are human cells. Advantageously, the cell viability within these synthetic living tissue structures ranges from about 70% up to about 100%, such as about 75%, about 80%, about 85%, about 90%, about 95%, about 98%, about 99%, about 99.5%, or about 99.9% after bioprinting, in comparison with the cell viability before printing.

In one embodiment, the structure comprises a cylinder/tube, and the fiber is substantially continuous through each layer of the cylinder. In an alternative embodiment, the structure comprises a planar sheet, and the fiber is substantially continuous throughout the planar sheet. In particularly preferred embodiments, the synthetic muscle structure exhibits contractile functionality, and the contractile functionality is determinable by a change in the diameter and/or circumference of said structure.

In another aspect, kits are provided comprising the subject synthetic tissues and tissue structures, along with appropriate packaging and/or instructions for use.

In another aspect, methods are provided for evaluating the effect of a test agent and/or condition on the contractile function of a mammalian muscle cell, comprising the steps of a) contacting the subject synthetic living tissue structure with the test agent and/or condition; and b) determining the effect of the agent and/or condition on the mammalian muscle cell by evaluating muscle function, e.g., by measuring dimensional changes (such as, e.g., the area, diameter and/or length of said structure), and/or by analyzing metrics such as cell viability, proliferation, polarization, and/or gene expression, including, e.g. expression of smooth muscle actin, calponin or caldesmon, binding of anti-smooth muscle cell antibody (ASMA), and the like. In preferred embodiments, the structure comprises a cylinder/tube, and the determining step comprises measuring a change in the diameter and/or circumference of the cylinder.

In preferred embodiments, the bioprinter dispenses the solidified biocompatible matrix comprising the plurality of mammalian cells through a single orifice. In particularly preferred embodiments, the single orifice is comprised within a print head such as that described and claimed in WO 2014/197999, the disclosure of which is herein incorporated by reference in its entirety.

DETAILED DESCRIPTION

Aspects of the present invention include synthetic living tissue structures comprising a synthetic tissue fiber comprising a plurality of mammalian cells dispensed from a bioprinter within a solidified biocompatible matrix, wherein the structural integrity and shape fidelity of the fiber is maintained upon and after deposition, and without any additional cross-linking step(s). In preferred embodiments, the invention provides synthetic living tissue structures comprising overlapping layers of a continuous synthetic tissue fiber, wherein the overlapping layers can be structurally discrete. Additional aspects of the invention include synthetic muscle tissue structures comprising two or more layers of a continuous synthetic tissue fiber comprising a plurality of mammalian muscle cells dispensed from a bioprinter within a solidified biocompatible matrix, for use in drug screening and evaluation of muscle function.

Figure 1:
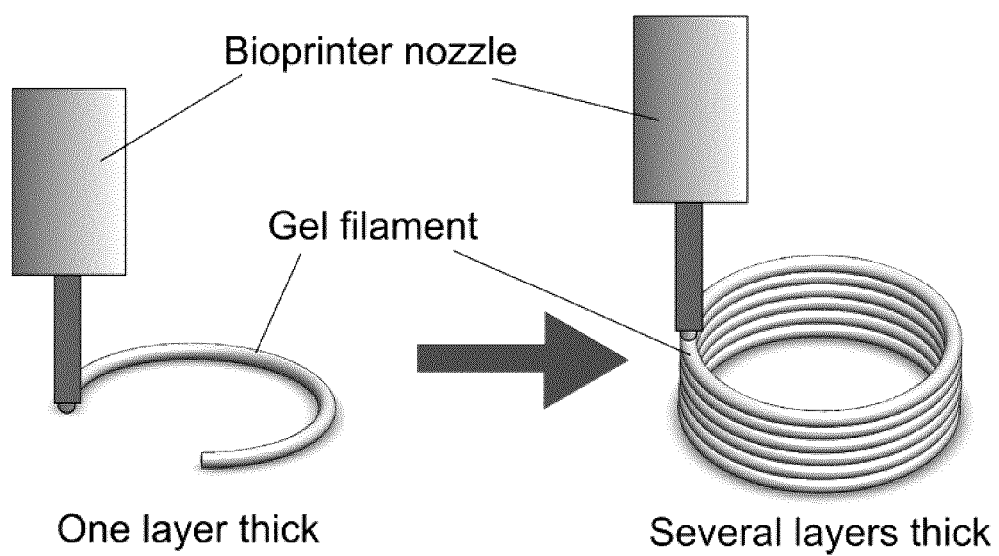
FIG. 1 is a schematic depiction of the layer-by-layer gel filament deposition process

As provided in FIG. 1, a solidified biocompatible matrix containing a plurality of mammalian cells, e.g. human smooth, skeletal or cardiac muscle cells, is dispensed from a bioprinter forming a synthetic tissue fiber on a deposition surface. As such, subsequent cross-linking or other solidification steps are unnecessary after dispensation of the already-solidified matrix from the printhead. In this way, the second and subsequent layers of the synthetic tissue fiber can be continuously deposited on top of the first layer to create a multi-layered structure, while maintaining the structural integrity and shape fidelity of each layer. This process continues for a defined period of time until a structure of the desired height is created.

The solidified biocompatible matrix may advantageously comprise alginate, or any other suitable biocompatible polymer that can be instantaneously solidified while dispensing from the printhead. The term "solidified" as used herein refers to a solid or semi-solid state of material that maintains its shape fidelity and structural integrity upon deposition. The term "shape fidelity" as used herein means the ability of a material to maintain its three dimensional shape. In some embodiments, a solidified material is one having the ability to maintain its three dimensional shape for a period of time of about 30 seconds or more, such as about 1, 10 or 30 minutes or more, such as about 1, 10, 24, or 48 hours or more. The term "structural integrity" as used herein means the ability of a material to hold together under a load, including its own weight, while resisting breakage, bending or collapse.

In some embodiments, a solidified biocompatible matrix is one having an elastic modulus greater than about 15, 20 or 25 kilopascals (kPa), more preferably greater than about 30, 40, 50, 60, 70, 80 or 90 kPa, still more preferably greater than about 100, 110, 120 or 130 kPa. Preferred elastic modulus ranges for the subject bioprinted synthetic tissue fibers include from about 15, 25 or 50 kPa to about 80, 100, 120 or 140 kPa.

In a preferred embodiment, the alginate-based matrix is printed and simultaneously crosslinked at the time of printing by contacting with a divalent cation crosslinking solution (e.g., a $CaCl_2$ solution) before or upon dispensation from the printhead. In particularly preferred embodiments, the alginate-based biocompatible matrix further comprises one or more physiological materials, as described in more detail herein. In further preferred embodiments, the solidified biocompatible matrix comprises a homogeneous composition of alginate throughout the radial cross section of each synthetic tissue fiber.

One of the primary advantages of the invention is that it is fabricated using a fiber-based 3D bioprinting approach, allowing the tissue to be easily fabricated into a ring shape, the height and width of which may be modified programmatically. It also provides a means of achieving repeated structural integrity and shape fidelity. If several tissues are printed using the same set of parameters, including layer thickness, number of layers, layer geometry, cell density, material composition, and cell type, they will all be substantially similar. A significant advantage of the invention is that the muscle cells retain, or re-develop their ability to contract after having been printed, enabling quantification of the effect different stimuli may have on muscle contraction and subsequent relaxation. Without being bound by theory, the multi-layered continuous fiber described herein may create a degree of confinement within the individual layers of the fiber, thereby promoting cell proliferation substantially along the direction of the fiber rather than across fibers, which in turn allows the cells to contract in a unified direction, as would occur in nature. To our best understanding, this is the first demonstration of contraction of muscle tissue fabricated using a continuous layer-by-layer deposition process.

In one embodiment, described herein are multi-layered tubes of muscle tissue. The tubes are created using a layer-by-layer deposition process by which muscle cells are dispersed within a solidified biocompatible matrix and bioprinted in a continuous fiber. In one embodiment, the fiber is deposited in a ring-like pattern to form a layer. These layers are stacked to form tubes, the height of which may be varied in a controlled way by changing the number of layers. Preferably, the matrix composition is physiologically compatible such that it allows the muscle cells to fully differentiate into a contractile phenotype. At the time of bioprinting, the tube is not contractile. To achieve contractibility, the tube is generally immersed in cell culture media after formation, and cultured in a cell culture incubator, typically for several days, over which time the cells re-gain their contractile ability. Once contractile, the tubes may be used to investigate the response of different stimuli to muscle contraction or relaxation, and this is done by measuring the change in tube diameter and/or circumference as it contracts or relaxes.

To prepare the muscle cells for bioprinting into a tubular structure, the cells must first be isolated and cultured in sufficient quantity to form the bioprinted structure. The cell density must be sufficiently high to provide measurable contraction and is typically in the range of 1 million to 100 million cells per mL of gel material. The muscle cells may be isolated from many different potential sources including: Donated human organs or tissue, differentiated embryonic or induced pluripotent stem cells, immortalized cell lines, or cells isolated or derived from animal tissue. The isolated cells are then suspended in non-solidified form and loaded into the bioprinter. Through this process the cells lose their contractile phenotype.

Figure 2:
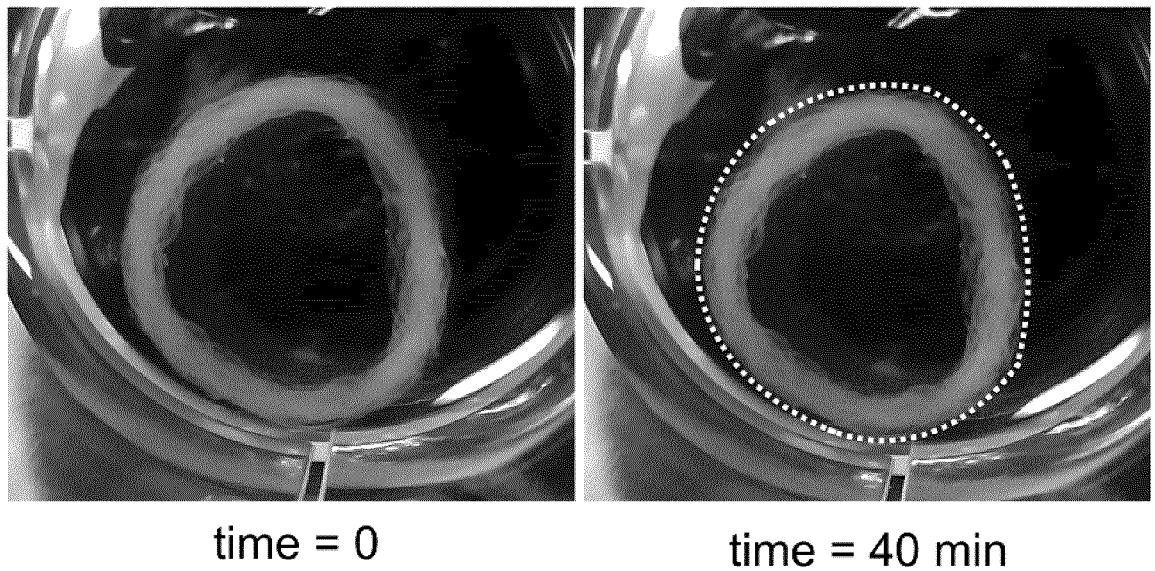
FIG. 2 shows two top down images of a smooth muscle ring before and after contraction.

After bioprinting, the muscle structure must be submersed in cell culture media and placed in a cell culture incubator with temperature and carbon dioxide level control. After some time in cell culture, typically several days, the cells will regain their contractile phenotype and acquire the ability to contract and relax. FIG. 2 shows a top down view of a muscle tube that has been cultured for 14 days and where contraction has been stimulated. Contraction takes place gradually over a 40 minute time period. The white dotted line indicates the diameter of the tube in a relaxed state. In a contracted state the tube has a smaller diameter, and this change is measurable. In this example histamine was used to initiate contraction, however many compounds or other stimuli may also initiate contraction. Some examples include: potassium chloride, acetylcholine, histamine, and electrical charge. In the preferred embodiment contraction and relaxation are measured by visual observation of changes in the diameter of the tube. This can be accomplished by observing the tube through a microscope objective lens at low magnification and recording video using a digital camera attached to the microscope. Alternatively, a camera with an appropriate level of magnification could be positioned above the smooth muscle tube such that video footage of the tube from a top down perspective is recorded. Software may be used to isolate the muscle tube structure in the video footage using an edge detection algorithm, or by manually defining the edge. The change in area, radius, diameter or circumference of the muscle tube may be quantified. There are many software tools available to easily accomplish this function, Mathworks Matlab being one example.

Figure 3:
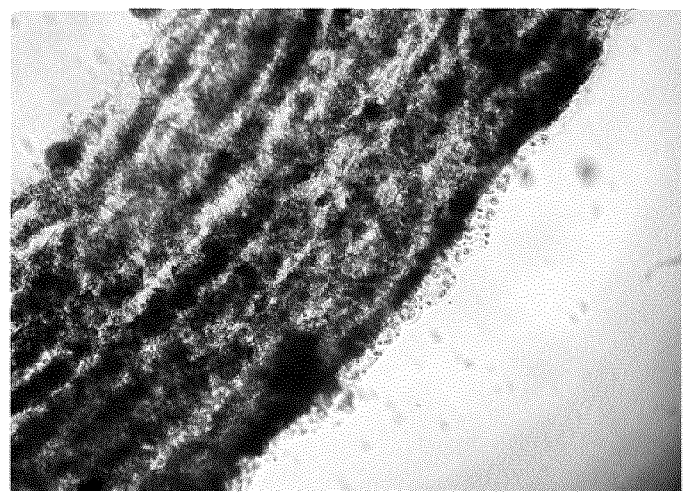
FIG. 3 is a top down transmission light micrograph showing smooth muscle cell growth within gel filaments.

FIG. 3 shows a transmission light micrograph of smooth muscle cells cultured inside filaments after 14 days. As shown therein, the smooth muscle cells tend to grow along the length of the fibers rather than across them, which may enable or enhance the coordinated contractile response. Without being bound by theory, if the muscle cells grew evenly in all directions a contractile response may not be possible, or not as significant. In preferred embodiments, therefore, the synthetic muscle tissue fiber maintains its structural integrity and shape fidelity after the bioprinting process, such that there is minimal integration of material between each successive layer. Preferably, the layers will be structurally discrete from each other as illustrated visually in FIG. 3. Most preferably, a biocompatible matrix material is employed that is physiologically compatible and avoids the need for a cross-linking step upon or after deposition of the fiber layer onto the printing surface.

Biocompatible Matrix Materials:

The solidified biocompatible matrix may comprise any of a wide variety of natural or synthetic polymers that support the viability of living cells, including, e.g., alginate, laminin, fibrin, hyaluronic acid, poly(ethylene) glycol based gels, gelatin, chitosan, agarose, or combinations thereof. In preferred embodiments, the solidified biocompatible matrix comprises alginate, or other suitable biocompatible polymers that can be instantaneously solidified while dispensing from the printhead. In further preferred embodiments, the solidified biocompatible matrix comprises a homogeneous composition of alginate throughout the radial cross section of each synthetic tissue fiber.

In particularly preferred embodiments, the solidified biocompatible matrix is physiologically compatible, i.e., conducive to cell growth, differentiation and communication. By "physiological matrix material" is meant a biological material found in a native mammalian tissue. Non-limiting examples of such physiological matrix materials include: fibronectin, thrombospondin, glycosaminoglycans (GAG) (e.g., hyaluronic acid, chondroitin-6-sulfate, dermatan sulfate, chondroitin-4-sulfate, or keratin sulfate), deoxyribonucleic acid (DNA), adhesion glycoproteins, and collagen (e.g., collagen I, collagen II, collagen III, collagen IV, collagen V, collagen VI, or collagen XVIII).

The biocompatible matrix may be composed of a wide variety of natural or synthetic polymers that support the growth and viability of living cells. Examples of such materials include but are not limited to: Collagen, alginate, laminin, elastin, fibrin, hyaluronic acid, poly(ethylene) glycol based gels, gelatin, chitosan, agarose, peptides, or combinations thereof. The diameter of the muscle tube is defined by the bioprinter and may be varied in a controlled way, but in preferred embodiments is in the range of 2 mm to 30 mm for the purpose of placing the tissue inside of a multi-well cell culture plate. Filament diameters will typically range from 10 μm to 300 μm.

Mammalian Cell Types:

Non-limiting examples of mammalian cells types that can be used in the subject meniscus implants include: smooth muscle cells, skeletal muscle cells, cardiac muscle cells, epithelial cells, endothelial cells, myoblasts, fibroblasts, embryonic stem cells, mesenchymal stem cells, induced pluripotent stem cells, differentiated stem cells, tissue-derived cells, and any combinations thereof. Cells can be obtained from donors (allogenic) or from recipients (autologous). Cells can also be from established cell culture lines, or can be cells that have undergone genetic engineering and/or manipulation to achieve a desired genotype of phenotype.

In one preferred embodiment, the synthetic tissue fibers comprise human muscle cells, e.g., smooth, skeletal and/or cardiac muscle cells, and/or myoblasts thereof. In one embodiment, the synthetic tissue structures further comprise at least one additional cell type, either dispersed within or disposed around the muscle tissue fibers, including, e.g. fibroblasts, endothelial cells, epithelial cells, stem cells, etc.

In some embodiments, cells can be obtained from a suitable donor, either human or animal, or from a subject into which the cells are to be implanted. Mammalian species include, but are not limited to, humans, monkeys, dogs, cows, horses, pigs, sheep, goats, cats, mice, rabbits, rats. In one embodiment, the cells are human cells. In other embodiments, the cells can be derived from animals such as, dogs, cats, horses, monkeys, or any other mammal.

Appropriate growth conditions for mammalian cells are well known in the art (Freshney, R. I. (2000) Culture of Animal Cells, a Manual of Basic Technique. Hoboken N.J., John Wiley & Sons; Lanza et al. Principles of Tissue Engineering, Academic Press; 2nd edition May 15, 2000; and Lanza & Atala, Methods of Tissue Engineering Academic Press; 1st edition October 2001). Cell culture media generally include essential nutrients and, optionally, additional elements such as growth factors, salts, minerals, vitamins, etc., that may be selected according to the cell type(s) being cultured. Particular ingredients may be selected to enhance cell growth, differentiation, secretion of specific proteins, etc. In general, standard growth media include Dulbecco's Modified Eagle Medium, low glucose (DMEM), with 110 mg/L pyruvate and glutamine, supplemented with 10-20% fetal bovine serum (FBS) or calf serum and 100 U/ml penicillin are appropriate as are various other standard media well known to those in the art. Growth conditions will vary dependent on the type of mammalian cells in use and tissue desired.

Additional sources of human cells include, but are not limited to, mesenchymal stem cells (MSCs). MSCs are attractive for regenerative medicine purposes as they can be isolated from patients and readily expanded for use as an autograft tissue replacement. Unlike donor allografts, recipient-derived MSC autografts have zero risk of inter-person disease transmission or immune-mediated tissue rejection. An additional advantage of MSCs is that the crucial factors for settlement and subsequent differentiation of MSCs into skeletal muscle cells have been identified. (Torihashi et al., *J. Biol. Chem.* 290:22771-81 (2015).

In one embodiment the muscle tube will contain an additional one or more cell types, such as fibroblasts, endothelial or epithelial cells, either located within the filament or attached to the outside of the filament.

Figure 4:
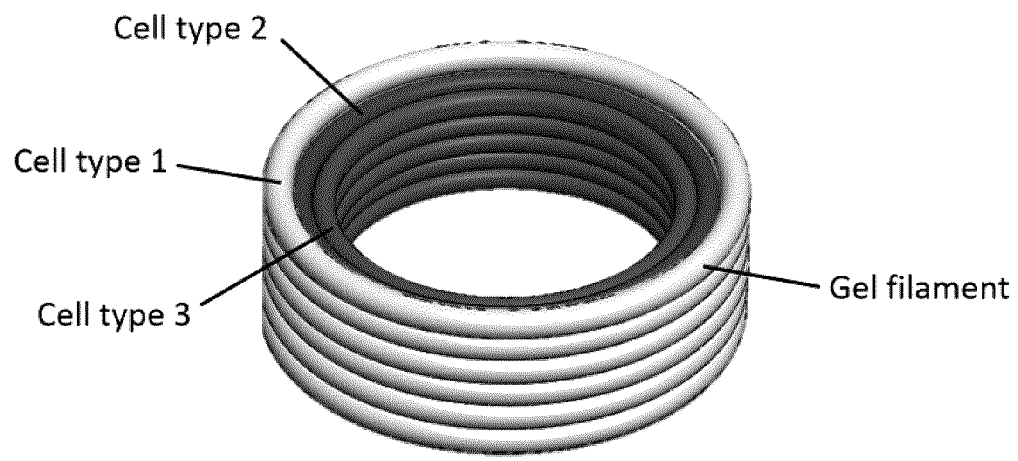
FIG. 4 is a schematic depiction of a coaxially arranged tube including smooth muscle cells and another cell type.

In another embodiment the one or more cell types are positioned on the outer and/or inner side of the muscle tube, such that the tube is coaxial, as shown in FIG. 4, where any of cell type 1, cell type 2, or cell type 3 are contractile muscle cells.

In yet another embodiment the one or more cell types are located above or below the muscle cells, forming a sandwich type structure (not shown).

Figure 5:
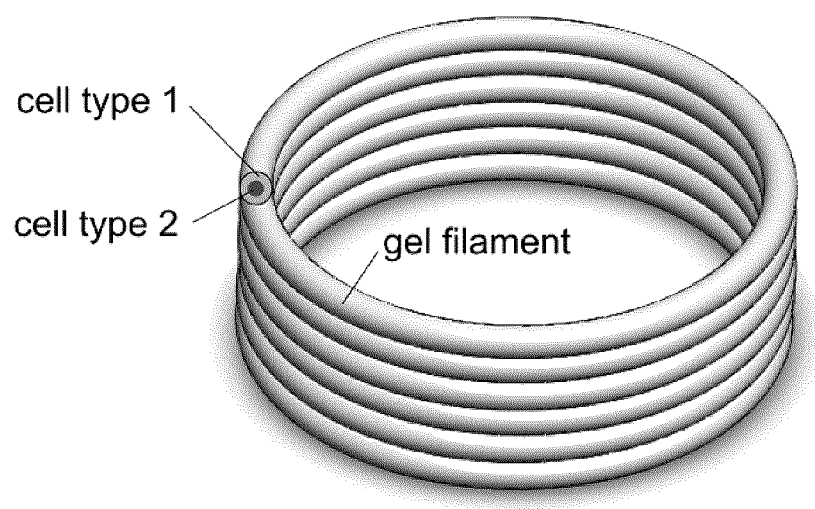
FIG. 5 is a schematic depiction of a tube composed of a gel filament that has a coaxial arrangement of smooth muscle cells and another cell type.

In yet another embodiment the one or more cell types are arranged within the filament such that one cell type surrounds the other cell type in a coaxial arrangement, as shown in FIG. 5, where either cell type 1 or cell type 2 are contractile smooth muscle cells.

In some embodiments after bioprinting is performed and the resulting muscle tube has been in cell culture for more than several hours, the filament is dissolved or otherwise removed, yielding a tube that is substantially free of non-cellular material, sometimes referred to as "scaffold free". Because the cells form an interconnected network, the overall structure of the muscle tube is maintained even after removal of the filament.

Methods of Screening

Aspects of the invention include methods for evaluating the effect of a test agent and/or condition on the contractile function of a mammalian muscle cell, comprising the steps of a) contacting the subject synthetic living tissue structure with the test agent and/or condition; and b) determining the effect of the agent and/or condition on the mammalian muscle cell by evaluating muscle function, e.g., by measuring dimensional changes (such as, e.g., the area, diameter and/or length of said structure), and/or by analyzing metrics such as cell viability, proliferation, polarization, and/or gene expression, including, e.g. expression of smooth muscle actin, calponin or caldesmon, binding of anti-smooth muscle cell antibody (ASMA), and the like. In preferred embodiments, the structure comprises a cylinder/tube, and the determining step comprises measuring a change in the diameter and/or circumference of the cylinder.

In some embodiments the muscle tube is used as a model for testing drug compounds for efficacy or toxicity.

In some embodiments the contraction of the muscle tube is measured by means of a force transducer.

In some embodiments additional metrics such as cell viability, proliferation, polarization, and/or gene expression are evaluated, including, e.g. expression of smooth muscle actin, calponin, and/or caldesmon, or binding of anti-smooth muscle cell antibodies (AMSA), or other proteins are measured.

Methods for Repairing a Muscle Defect

Aspects of the invention include methods for repairing and/or replacing at least a portion of a muscle in a subject. Any of the synthetic muscle fiber tissues and tubes described herein can be implanted into a subject in need thereof in order to accomplish muscle repair and/or regeneration. Accordingly, methods of repairing a muscle defect or promoting muscle regeneration in a subject are also provided herein. In one embodiment, a method comprises implanting a synthetic muscle tissue structure as described herein into a defect site in need of muscle repair or regeneration.

The term "subject" includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are included. In one embodiment, the subject is a mammal. In one embodiment, the subject is a human subject.

In some embodiments, a method can comprise securing a muscle implant, or a portion thereof, at a defect site, and/or securing one or more portions of a muscle implant to at least one anatomical structure within a subject. In some embodiments, a method can further comprise removing at least a portion of a defective muscle from the subject.

All patents and patent publications referred to herein are hereby incorporated by reference.

Certain modifications and improvements will occur to those skilled in the art upon a reading of the foregoing description. It should be understood that all such modifications and improvements have been deleted herein for the sake of conciseness and readability but are properly within the scope of the following claims.

The invention claimed is:

1. A method for evaluating the effect of a test agent and/or condition on the contractile function of a mammalian muscle cell, comprising the steps of a) contacting a synthetic living tissue structure comprising a continuous fiber of mammalian muscle cells dispensed from a bioprinter in overlapping layers with the test agent and/or condition, wherein said fiber comprises a solidified biocompatible matrix comprising said cells and said solidified biocompatible matrix is homogeneous in radial cross-section throughout said fiber and is capable of maintaining the structural integrity and shape fidelity of said fiber upon deposition and without any additional cross-linking steps following deposition, and wherein the structural integrity of the fiber is maintained between each layer and the layers are structurally discrete; and b) determining the effect of said agent and/or condition on said mammalian muscle cells by measuring a dimensional change in the structure.

2. The method according to claim 1, wherein said structure comprises a cylinder/tube, and said determining step comprises measuring a dimensional change in the area, diameter and/or circumference of said cylinder.

3. The method according to claim 1, wherein said structure comprises a planar sheet, and said determining step comprises measuring a dimensional change of said planar sheet.

4. The method according to claim 1, wherein said fiber is continuously bioprinted through at least three, four, five, six, seven, eight, nine, ten or more layers of said structure.

5. The method according to claim 1, wherein said biocompatible matrix is physiologically compatible.

6. The method according to claim 1, wherein said muscle cells are smooth muscle cells.

7. The method according to claim 1, wherein said muscle cells are skeletal muscle cells.

8. The method according to claim 1, wherein said muscle cells are cardiac muscle cells.

9. The method according to claim 1, wherein said structure comprises at least one additional cell type.

10. The method according to claim 8, wherein said at least one additional cell type is dispersed within said fiber.

11. The method according to claim 8, wherein said at least one additional cell type is disposed around the outside of said fiber as an external/second layer.

12. The method according to any one of the preceding claims, wherein said mammalian cells are human cells.

13. The method of claim 1, wherein said fiber has a diameter range from 10 µm to 300 µm.

* * * * *